(12) United States Patent
Clark et al.

(10) Patent No.: US 9,713,703 B2
(45) Date of Patent: Jul. 25, 2017

(54) DEVICES AND METHODS FOR TREATING A LUNG

(71) Applicant: Boston Scientific Scimed, Inc., Maple Grove, MN (US)

(72) Inventors: Bryan Allen Clark, Forest Lake, MN (US); Brian L. Schmidt, White Bear Lake, MN (US); Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 266 days.

(21) Appl. No.: 14/455,560

(22) Filed: Aug. 8, 2014

(65) Prior Publication Data

US 2015/0045774 A1    Feb. 12, 2015

Related U.S. Application Data

(60) Provisional application No. 61/864,075, filed on Aug. 9, 2013.

(51) Int. Cl.
*A61M 37/00* (2006.01)
*A61B 17/12* (2006.01)
*A61B 17/00* (2006.01)

(52) U.S. Cl.
CPC ......... *A61M 37/00* (2013.01); *A61B 17/1219* (2013.01); *A61B 17/12104* (2013.01);
(Continued)

(58) Field of Classification Search
CPC ............. A61M 37/00; A61B 17/12104; A61B 17/12186; A61B 17/1219;
(Continued)

(56) References Cited

U.S. PATENT DOCUMENTS 6,063,113 A    5/2000  Kavteladze et al.
7,300,428 B2  11/2007  Ingenito
(Continued)

FOREIGN PATENT DOCUMENTS

WO    WO-03/020338 A2    3/2003
WO    WO-2008/039827 A2   4/2008

OTHER PUBLICATIONS

Taneja, Amit, Bronchoscopic Interventions in the Management of Chronic Obstructive Pulmonary Disease, 2013, 145-151, 19(2), Curr Opin Pulm Med.

(Continued)

*Primary Examiner* — Bhisma Mehta
*Assistant Examiner* — Brandy S Lee
(74) *Attorney, Agent, or Firm* — Bookoff McAndrews, PLLC

(57) ABSTRACT

Exemplary embodiments of devices and methods for treating a lung including, for example, treatments for chronic obstructive pulmonary disease are disclosed. A device may include a plurality of media and a deployment member. The media may be configured for deployment into one or more airways of a lung. The deployment member may be configured for insertion into or proximate the one or more airways of the lung. Also, the deployment member may be configured to deploy the plurality of media substantially simultaneously. Further, the plurality of media may be configured to be retained within the one or more airways of the lung.

11 Claims, 9 Drawing Sheets

(52) U.S. Cl.
CPC ............... *A61B 17/12186* (2013.01); *A61B 2017/00893* (2013.01); *A61B 2017/00898* (2013.01); *A61B 2017/1205* (2013.01)

(58) Field of Classification Search
CPC A61B 2017/00893; A61B 2017/00898; A61B 2017/1205; A61B 17/12022
See application file for complete search history.

(56) References Cited

U.S. PATENT DOCUMENTS

| | | | |
|---|---|---|---|
| 7,462,162 B2 | 12/2008 | Phan et al. | |
| 7,549,984 B2 | 6/2009 | Mathis | |
| 7,553,810 B2 | 6/2009 | Gong et al. | |
| 7,608,579 B2 | 10/2009 | Gong et al. | |
| 7,654,998 B1 | 2/2010 | Ingenito | |
| 7,654,999 B2 | 2/2010 | Ingenito | |
| 8,361,484 B2 | 1/2013 | Ingenito et al. | |
| 2001/0056274 A1* | 12/2001 | Perkins | A61B 50/30 604/516 |
| 2004/0091543 A1* | 5/2004 | Bell | A61B 17/12022 424/489 |
| 2005/0137518 A1* | 6/2005 | Biggs | A61B 17/12104 604/8 |
| 2007/0134346 A1* | 6/2007 | Harlow | A61K 9/0024 424/549 |
| 2010/0040538 A1 | 2/2010 | Ingenito et al. | |
| 2011/0071495 A1 | 3/2011 | Tekulve | |
| 2011/0251592 A1 | 10/2011 | Biggs et al. | |
| 2012/0053513 A1 | 3/2012 | Tada et al. | |
| 2012/0053566 A1 | 3/2012 | Tada et al. | |

OTHER PUBLICATIONS

Lund et al., Airway Stenting* Applications and Practice Management Considerations, Feb. 2007, 579-587, 131(2), Chest.

* cited by examiner

DEVICES AND METHODS FOR TREATING A LUNG

CROSS REFERENCE TO RELATED APPLICATIONS

This application claims the benefit of U.S. Provisional Application No. 61/864,075, filed Aug. 9, 2013, the disclosure of which is incorporated herein by reference in its entirety.

TECHNICAL FIELD

The disclosed embodiments relate to devices and methods for treating a lung and, in an embodiment, chronic obstructive pulmonary disease (COPD). More particularly, the present disclosure relates to devices and methods of manipulating airways of lungs.

BACKGROUND

Chronic obstructive pulmonary disease (COPD) is a serious progressive lung disease which makes it harder to breath. It currently affects over fifteen million people in the United States alone and is currently the third leading cause of death in the country. The overwhelming primary cause of COPD is inhalation of cigarette smoke, responsible for over 90% of COPD cases. The economic and social burden of the disease is both substantial and increasing.

FIG. 1 illustrates the anatomy of healthy lungs 100 including the trachea or wind pipe 102. As air flows in through the nose and mouth of an individual, the trachea 102 delivers the air to the lungs 100 for respiratory functions. The trachea 102 divides into the right main stem bronchus 104 and the left main stem bronchus 108. The right main stem bronchus 104 enters the right lung 106-1 and the left main stem bronchus 108 enters the left lung 106-2. In the lungs 100, both the right main stem bronchus 104 and the left main stem bronchus 108 divide into a plurality of bronchi 110, which further divide into a plurality of smaller airways referred to as bronchioles 112. Finally, these bronchioles 112 terminate into a plurality of alveoli 114. The alveoli 114 are small elastic air sacs which enable gas exchange. That is, they permit oxygen diffusion into the blood stream, and receive and expel $CO_2$ during exhalation.

During inhalation, air is delivered to the lungs 100 and is received within the alveoli 114 via the bronchial passages or airways including the right and left main stem bronchi 104 and 108, bronchi 110, and bronchioles 112. The air inflates the alveoli 114, which later recoils to exhale air. This operation of lungs 100 during the inhalation and exhalation of air may be disturbed due to certain malfunctions or diseases, such as chronic obstructive pulmonary disease (COPD).

COPD includes both chronic bronchitis and emphysema. FIG. 2A illustrates a left lung 200 suffering from chronic bronchitis, which is shown in more detail in FIG. 2B. Chronic bronchitis is characterized by chronic cough with increased sputum, expelled mucus and saliva, production. Chronic bronchitis also causes airway inflammation 204, mucus hyper-secretion 206 that lines airway walls, airway hyper-responsiveness, and eventual fibrosis of the airway walls, which causes a serious limitation on airflow and gas exchange. The diameter of airways may also be reduced by one or more bronchoconstrictions 208, which constrict the airways in the lungs due to the tightening of surrounding smooth muscle. Airway restrictions may significantly increase the resistance to airflow through the airways, thereby preventing air from reaching or being expelled from alveoli 214. This resistance may be calculated according to Poiseulle's Equation (Equation 1) relating to laminar flow through a tubular member:

$$R = \frac{8\eta l}{\pi r^4} \quad (1)$$

Where:
R=Resistance to flow
$\eta$=viscosity of fluid (here, air)
l=length of tube (i.e., airway)
r=radius of the tube (i.e., airway)

Equation 1 indicates that the resistance to the flow of fluid, i.e., air, is proportional to the fourth power of the radius of the tube, i.e., airway. Thus, if the radius of the airway is reduced to half, the resistance to airflow in the lungs becomes 16 times the normal resistance. This increased resistance or limitation to airflow due to chronic bronchitis causes insufficient removal of carbon dioxide ($CO_2$) from the lung 200, and manifests into hypercapnia (high blood gas levels of carbon dioxide). Hypercapnia leads to acidosis (lowering of blood pH levels), which correlates to a significantly greater risk of mortality.

There are thousands of small airways in the lungs and expanding or maintaining patency of these airways may facilitate better ventilation. However, due to the vast number of small airways, expansion or patency of these adversely affected airways may be very difficult. Moreover, breathing causes significant expansion and contraction of airways which may make deployment of rigid or semi-rigid airway support structures challenging and possibly impractical.

FIG. 3A illustrates a left lung 300 suffering from emphysema, which is shown in more detail in FIG. 3B. Emphysema is characterized by the destruction of the lung parenchyma, the functioning portions of the lung. The parenchyma includes alveoli walls, bronchioles, and bronchi. Destruction of the lung parenchyma may lead to loss of elastic recoil and tethering (i.e., ability to hold open walls of airways, including the bronchioles 112, leading to the alveoli 314 throughout much of inhalation and expiration), which maintains airway patency. Unlike larger lung airways, the bronchioles 112 are not supported by cartilage and thus have little intrinsic support. As a result, the bronchioles 112 are susceptible to collapse or reduce in diameter when destruction of tethering occurs, particularly during exhalation. A collapsed airway 304 is shown in FIG. 3B.

This loss in elastic recoil of an airway 304 leads to trapping of air and hyperinflation of the lungs, and also causes poor gas exchange. As a result, the alveoli 314 deteriorate into large, irregular pockets with gaping holes in their inner walls. This damages the alveoli 314 and reduces the surface area of the lungs and, in turn, the amount of oxygen that reaches an individual's blood stream.

Additionally, it may cause an increase in residual volume of the lungs, resulting in increased $CO_2$ retention and reduced oxygen supply to the damaged alveoli 306. One existing approach to treat emphysema is performing lung volume reduction surgery, which removes or kills a portion of a diseased lung to allow greater expansion of remaining lung tissue. However, this approach is restricted to the upper portions (e.g., airways) of the lungs and poses a substantial risk of serious post-operative complications due to its invasive nature. Other existing approaches involve less-invasive techniques, including the use of endobronchial valves, reduction coils, heated water vapour, cryogenic therapy, and polymeric injections. However, the success of these approaches is heavily reliant upon the lack of collateral flow (shown in FIG. 4) between the targeted region of the lung and adjacent, non-targeted regions of the lung. For example, if an endobronchial valve or occlusion device 402 is implanted in a target airway 404 to prevent airflow into that region of the lung, if a collateral flow pathway 406 exists distal to the endobronchial valve 402, then airflow can still occur in the targeted region of the lung and atelectasis fails to fully occur. This limitation is common among a large portion of COPD patients.

Moreover, when a severe COPD patient is placed under exercise intensity, e.g., the patient is stressed due to exercise, dynamic hyperinflation occurs in the lungs due to which the patient is unable to expire quickly enough, causing further inflation of lungs with each successive breath. Additionally, the patient may suffer from dyspnea (i.e., significant shortness of breath), which deteriorates the patient's quality of life.

It may, therefore, be beneficial to provide a less-invasive technique of appropriately manipulating airways of the lungs for treating COPD, or other lung conditions.

SUMMARY

The disclosed embodiments relate to devices and methods for manipulating lung airways in a patient for treating, for example, chronic obstruction pulmonary diseases. One exemplary embodiment may include a device for treating lung disease. The device may include a plurality of media configured for deployment into one or more airways of the lung. Additionally, the device may include a deployment member configured for insertion into or proximate the one or more airways of the lung. The deployment member may be configured to deploy the plurality of media substantially simultaneously. Also, the plurality of media may be configured to be retained within the one or more airways of the lung.

Additionally, the device may include one or more of the following features: wherein at least one of the plurality of media may include an expansion element such that upon activation, the at least one of the plurality of media may radially expand; wherein at least one of the plurality of media may be drug-eluting; wherein each of the plurality of media may be an air-blocking media such that upon deployment, the plurality of media may be configured to inhibit the passage of air through the one or more airways in which the media are retained; wherein each of the plurality of media may include a spherical shape, a cylindrical shape, an ovular shape, an irregular shape, or a cubical shape; wherein each of the plurality of media may be a flow-through media such that upon deployment, the plurality of media may be configured to allow the passage of air through the one or more airways in which is the media are retained; wherein each of the plurality of media may include a porous frame; wherein the porous frame may include at least one of the following: a starburst shape, a buckey-ball shape, a cubical shape, an ovular shape, a spherical shape, and an irregular shape; and wherein substantially simultaneous deployment of the plurality of media includes deploying the plurality of media between zero and one seconds.

Another exemplary embodiment may include a device for treating lung disease. The device may include a first plurality of media, a second plurality of media, and a deployment member. The first plurality of media may be configured for deployment into one or more airways of a lung. Also, the second plurality of media may be configured for deployment into the one or more airways of the lung. The deployment member may be configured for insertion into the one or more airways of the lung. Additionally, the deployment member may be configured to deploy each of the first plurality of media substantially simultaneously, and may be configured to deploy each of the second plurality of media substantially simultaneously. Also, each of the first and second pluralities of media are configured to be retained within the one or more airways of the lung.

Additionally, the device may include one or more of the following features: wherein each of the first plurality of media has a first size, and each of the second plurality of media has a second size, wherein the first size is smaller than the second size; wherein at least one of the first plurality of media and/or at least one of the second plurality of media includes an expansion element such that upon activation, the at least one of the first plurality of media and/or the at least one of the second plurality of media radially expands; wherein substantially simultaneous deployment of the first plurality of media includes deploying the first plurality of media between zero and one second, and wherein substantially simultaneous deployment of the second plurality of media includes deploying the second plurality of media between zero and one second; wherein each of the first and second pluralities of media is an air-blocking media such that upon deployment, the first and second pluralities of media are configured to inhibit the passage of air through the one or more airways in which the media are retained; wherein each of the first and second pluralities of media is a flow-through media such that upon deployment, the first and second pluralities of media are configured to allow the passage of air through the one or more airways in which the media are retained; wherein the deployment device includes a balloon catheter; and the device further including a third plurality of media configured for deployment into the one or more airways of the lung, the deployment member being further configured to deploy each of the third plurality of media substantially simultaneously.

An exemplary method for treating lung disease may include inserting a deployment member into or proximate one or more airways of the lung. The method may further include deploying a first plurality of media configured for deployment into a portion of the lung substantially simultaneously. The first plurality of media may be configured to be retained within one or more airways of the lung.

Additionally, the method may include one or more of the following features: deploying a second plurality of media configured for deployment into the one or more airways of the lung substantially simultaneously, where the second plurality of media may be configured to be retained within one or more airways of the lung; and wherein deploying the first plurality of media substantially simultaneously includes deploying the first plurality of media between zero and one second.

The above summary of exemplary embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The drawings illustrate the design and utility of exemplary embodiments of the present disclosure, in which similar elements are referred to by common reference numerals. In order to better appreciate how the above-disclosed and other advantages and objects of the present disclosure are obtained, a more detailed description of the present embodiments will be rendered by reference to the accompanying drawings. Understanding that these drawings depict only exemplary embodiments of the disclosure and are not therefore to be considered limiting in scope, the disclosure will be described and explained with additional specificity and detail through the use of the accompanying drawings in which.

DETAILED DESCRIPTION OF EXEMPLARY EMBODIMENTS

Figure 5:
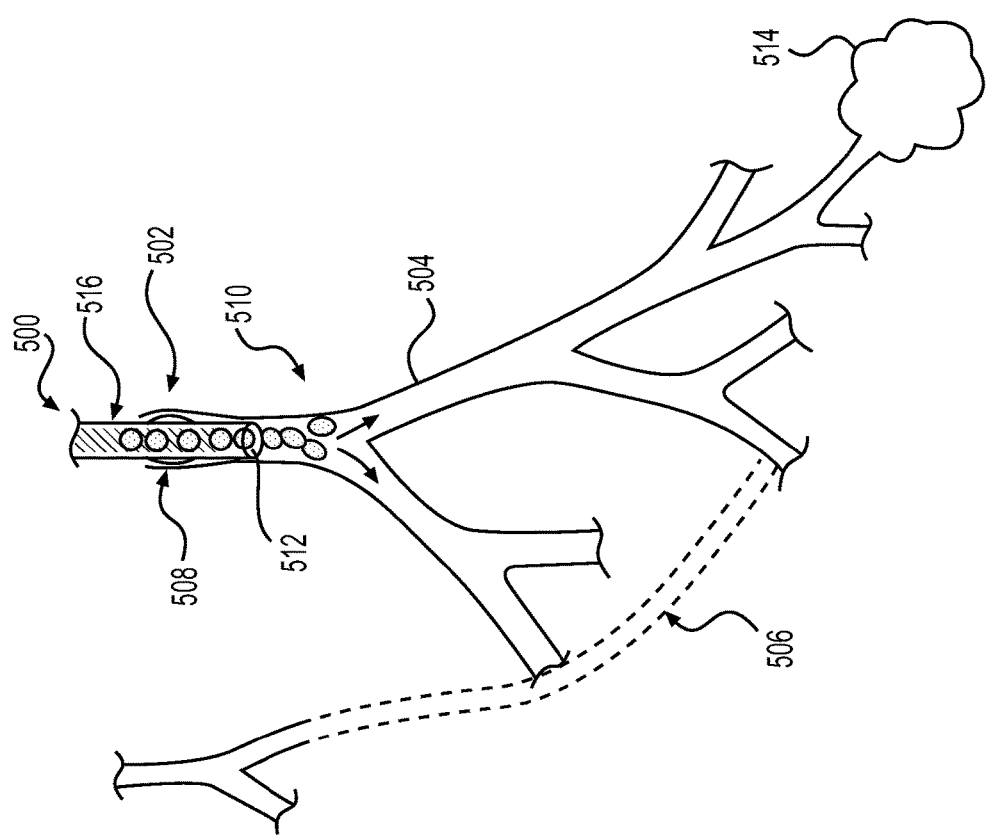
FIG. 5 illustrates a device for deploying exemplary media in the airway of an unhealthy lung according to a first embodiment of the present disclosure.

FIG. 5 illustrates a device 500 for deploying exemplary air-blocking media 510 in the airway 504 of a lung suffering from, for example, COPD according to a first exemplary embodiment of the present disclosure. The device 500 includes a deployment member 502 configured for insertion into or proximate airways 504 in communication with a diseased portion of a lung of a patient. The deployment member 502 may be a steerable delivery catheter, such as a balloon catheter 516, to target particular diseased portions of the lung. Alternatively, the deployment member 502 may be a steerable catheter, bronchoscope, or alternative introducer sheath with or without a balloon. The deployment member 502 may have a cross-sectional configuration adapted to be received in the airway 504. The cross-section of the deployment member 502 may be substantially circular; however, other suitable cross-sectional shapes, for example, elliptical, oval, polygon, irregular, etc., may be employed.

The balloon catheter 516 includes a balloon 508 that is configured to transition between a first substantially deflated configuration and a second substantially expanded configuration. The balloon catheter 516 may be introduced into or proximate the airway 504 in communication with a diseased portion of a lung while in the first substantially deflated configuration. Upon reaching a targeted location within or proximate a selected airway 504, the balloon 508 may be inflated via an inflation lumen (not shown) extending through balloon catheter 516 such that balloon 508 expands to the second substantially expanded configuration and contacts an inner surface of the selected airway 504. In this way, balloon 508 may stabilize balloon catheter 516 and prevent media 510 from travelling up the airways 504, proximally of the balloon 508.

In an exemplary embodiment, the balloon catheter 516 includes one or more lumens 512 extending from the distal end to a proximal portion (not shown) of the balloon catheter 516. At least one lumen 512 is configured to deploy media 510 therethrough. For example, the lumen 512 may be configured to deliver a plurality of media 510 in batches. That is, lumen 512 may deliver a first batch (i.e., plurality) of media 510 substantially simultaneously, and subsequently, lumen 512 may deliver a second batch (i.e., plurality) of media 510 substantially simultaneously. Each batch may include any number of media 510. For example, each batch may include a few, hundreds, or even thousands of media 510. Also, in this context, it is understood that substantially simultaneously includes a single or continuous activation of deployment member 502 which delivers media 510 from the lumen 512, although not all media 510 may exit the distal end of lumen 512 at the exact same time. Indeed, substantially simultaneous deployment of media 510 may include deploying the media 510 between zero and thirty minutes. Further, substantially simultaneous deployment of media 510 may include deploying the media 510 between zero and five minutes, between zero and one minute, or between zero and one second. For example, a user may activate the deployment member 502 a first time, so as to deploy a first batch (i.e., plurality) of media 510. Then, a user may activate the deployment member 510 a second time (or any number of additional times), so as to deploy a second batch (i.e., plurality) of media 510. Optionally, deployment member 502 may be configured to deliver media 510 via a pressurized fluid source (not shown). That is, deployment member 502 may be in communication with a pressurized fluid (e.g., air) which may be fluidly coupled to lumen 512 such that the pressurized fluid may aid in moving media 510 out of the distal end of lumen 512. That is, the source of pressurized fluid may assist in "pushing" media 510 out of the lumen 512, thereby achieving better penetration depth of the media 510 into the airway 504.

Any number of batches of the media 510 useful to achieve atelectasis may be deployed via lumen 512. Additionally, it is understood that the batches, e.g. the first and second batches of media 510, may be sized differently. That is, the first batch of media 510 may have a first dimension (e.g., diameter) whereas the second batch of media 510 may have a second dimension (e.g., diameter) larger than the first dimension. The dimensions of the batches of media 510 may be selected such that upon deployment in the airway 504, the media 510 block (i.e. occlude) airway 504. Alternatively, the dimensions of media 510 may be selected such that upon deployment in the airway 504, a plurality of media 510 may be configured to interlock and span the airway 504 so as to collectively block (i.e. occlude) the airway 504. In this way, progressively larger media 510 may be introduced into airway 504 to occlude progressively larger portions of airway 504. Said differently, smaller media 510 (e.g., media 510 in a first batch) may travel further distally through airway 504 of a patient while larger media 510 (e.g., media in a second batch) may not travel as far.

The media 510 may be made of a biocompatible polymer or metal, or a combination thereof. Optionally, media 510 may be manufactured of an expandable polymer so as to include an expansion element, which expands radially outward once the media 510 are deployed in the airway 504, e.g., after coming in contact with humidity in the airway 504 causing swelling of the polymer.

Also, the media 510 may be configured to have other suitable shapes including, but not limited to, cubical, triangular, cylindrical, and irregular shapes. It is understood than any three dimensional shape sized so as to occlude airway 504 may be employed. That is, any air-blocking shape configured to obstruct airway 504 may be used. Further, the media 510 may be coated or impregnated with a drug, such as corticosteroid, which functions to reduce airway inflammation. Alternatively, other types of drugs, such as antibacterial agents, mucolytic agents, bronchodilators, or other drugs may be coated on the media 510 for treating airway 504.

During operation, the deployment member 502 may be advanced through a natural opening of the body (e.g., via a mouth or nose) into or proximate the airway 504 of the lung of a patient, and positioned adjacent to the desired treatment region using, e.g., a bronchoscope. Alternatively, the deployment member 502 may be introduced without the use of a bronchoscope or similar device, or the deployment member 502 may be the bronchoscope or similar device itself. Once positioned, the balloon 508 may be inflated to contact the interior walls of the airway 504 and to seal the airway 504 to prevent media 508 from travelling proximate of balloon 508 into adjacent regions of the lung not intended to be treated during the procedure. In an exemplary embodiment in which media 510 are to be deployed with the assistance of pressurized fluid (e.g., air), the balloon 508 may also prevent pressurized fluid from travelling proximally of balloon 508. That is, balloon 508 may assist in directing pressurized fluid such that media 510 may achieve better penetration depth into the airway 504.

After the balloon 508 seals the airway 504, the media 510 are injected into the airway 504 in batches or individually through the lumen 512. Optionally, deployment may be assisted by applying pressurized air to the target regions of the lung. Alternatively, the media 510 may be deployed with a fluid or gel that contains drugs, such as antibiotics, intended to reduce infections in the acute phase while atelectasis occurs. Over time the fluid or gel may get absorbed into the airway 504 wall.

Figure 1:
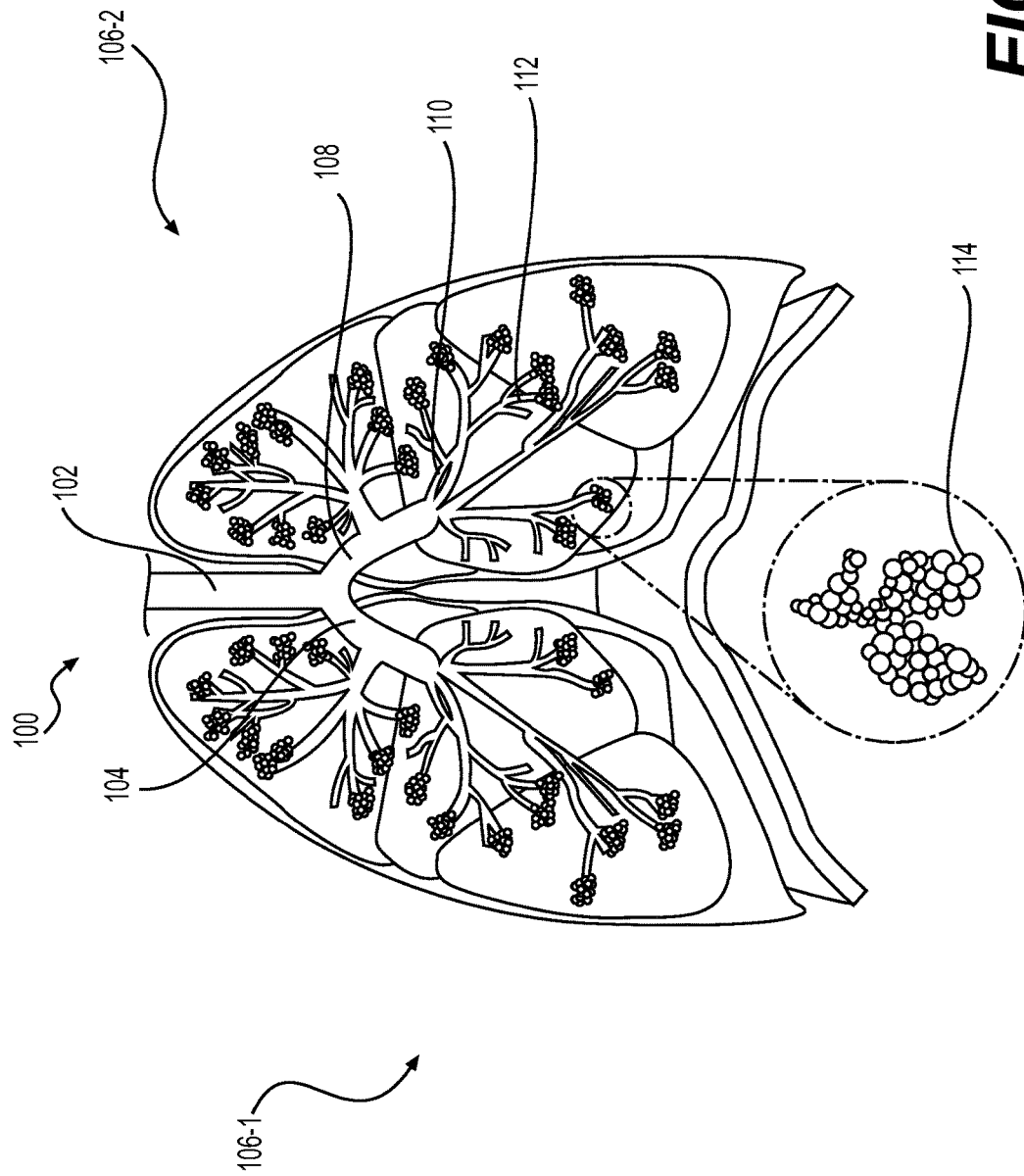
FIG. 1 illustrates the anatomy of healthy lungs in accordance with the present disclosure.
Figure 2B:
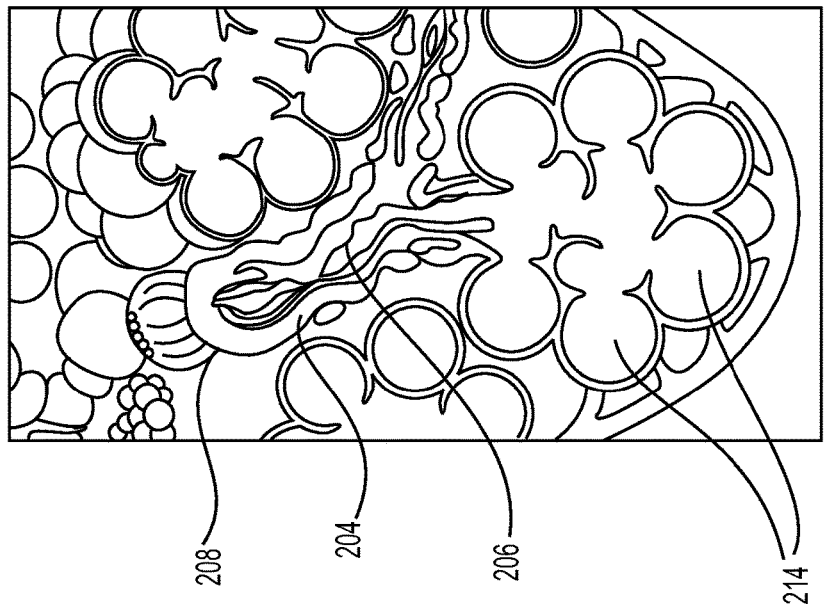
FIGS. 2A and 2B illustrate a left lung suffering from a first chronic obstructive pulmonary disease.
Figure 2A:
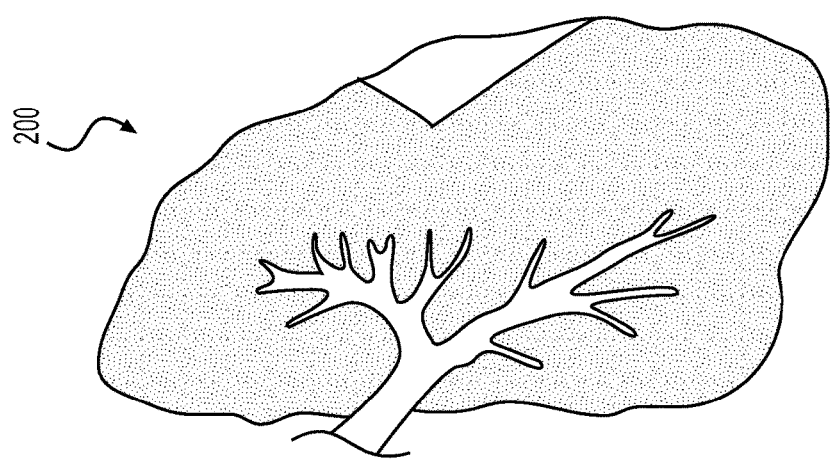
Figure 3B:
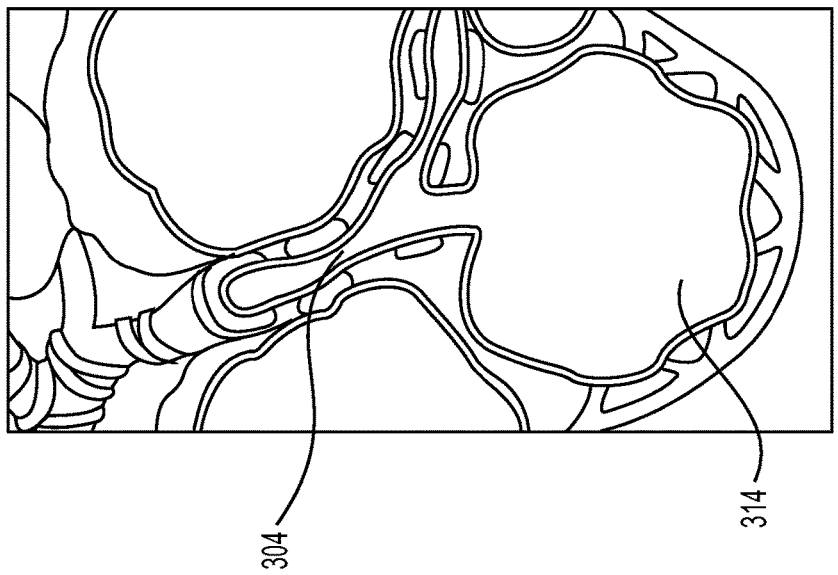
FIGS. 3A and 3B illustrate a left lung suffering from a second chronic obstructive pulmonary disease.
Figure 3A:
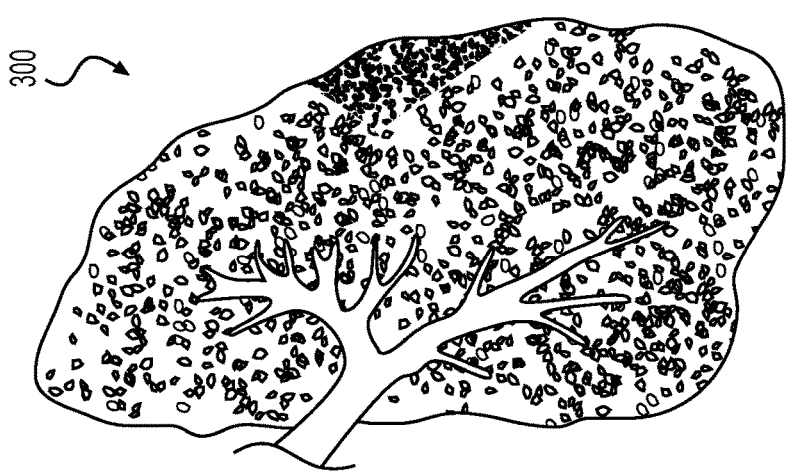
Figure 4:
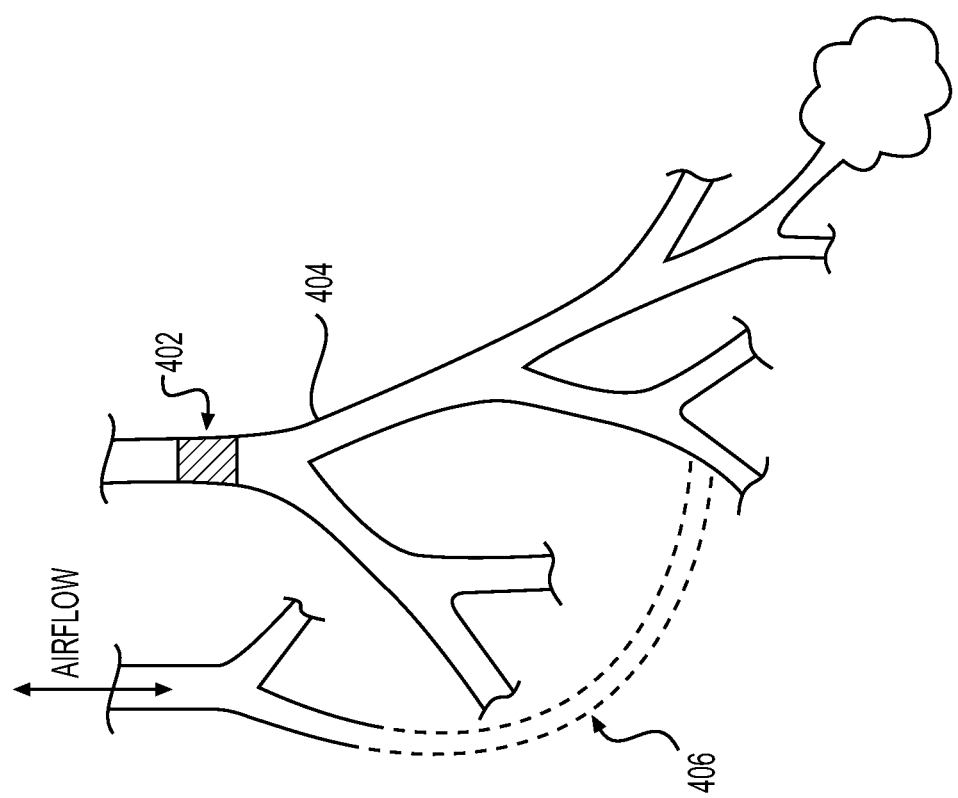
FIG. 4 illustrates a prior art device for treatment of an unhealthy target region of a lung.
Figure 6:
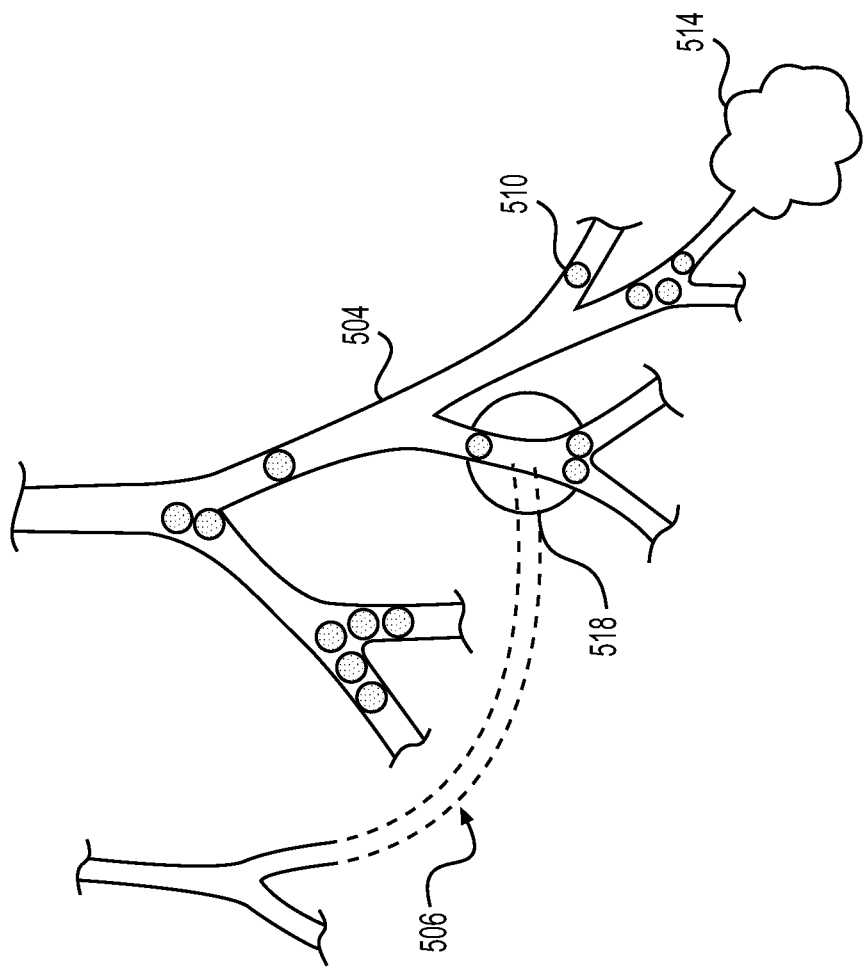
FIG. 6 illustrates the exemplary media deployed in the airway of the lung of FIG. 5 according to the first embodiment of the present disclosure.

FIG. 6 depicts a plurality of media 510 deployed at different points within the airway 504 to prevent (or at least reduce) airflow in different regions of a lung. The variable sizes of the media 510, which have a cross-sectional diameter of approximately the same as that of respective airway 504 into which it is received, facilitates stable retention of the media 510 in the airway 504 and blocks the passage of air. Consequently, the effect of a collateral flow channel 506 into the target airway 504 is significantly reduced. That is, since only a small portion of airway 504 receives collateral flow during inhalation, e.g., collateral flow area 514, only the collateral flow area 518 may be prevented from complete atelectasis. Said differently, in contrast to the prior art embodiments shown in FIG. 4 in which collateral channel 406 may deliver air to a large portion of airway 404 distal of endobronchial valve or occlusion device 402, thereby reducing the effectiveness of endobronchial valve or occlusion device 402, the present exemplary embodiment limits the amount of air that may be delivered to the airway 504, thereby enabling vastly improved atelectasis of airway 504.

Figure 7:
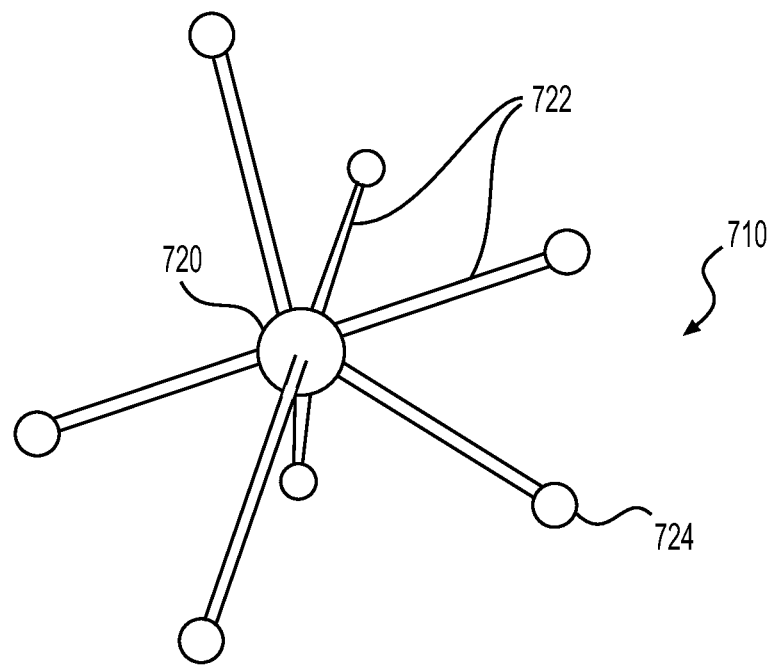
FIG. 7 illustrates an alternative exemplary media according to a second embodiment of the present disclosure.
Figure 8:
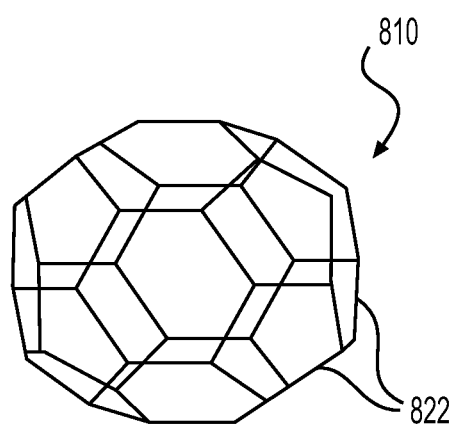
FIG. 8 illustrates another alternative, exemplary media according to the second embodiment of the present disclosure.

FIG. 7 illustrates an alternative exemplary media 710 according to a second exemplary embodiment of the present disclosure. Media 710 are configured to maintain patency of an airway of a patient, that is, they are flow-through media. That is, rather than occlude an airway like media 500 according to the first exemplary embodiment, media 710 may be designed to promote the flow of fluid (e.g., air) through the airway of a patient. The media 710 includes a stent-like structure having a starburst shape. As shown, the media 710 includes a central base 720, arms 722 extending radially outwards from the outer surface of the base, and contact members 724, each connected to a distal end of the arms 722. Alternatively, as shown in FIG. 8, flow-through media 810 including a porous frame having interconnecting arm members 822, which define large openings therebetween may be used to maintain airway patency. Media 810 may have a buckey-ball, for example, including a porous frame surrounding a hollow core (e.g., a geodesic form) shaped design as shown, or alternatively media 810 may be configured to have different hollow framed shapes including, but not limited to, cubical, ovular, spherical, cylindrical, and/or irregular shapes. It is understood that media 710, 810 may have any flow-through shape configured to maintain airway patency.

Returning to FIG. 7, the cross-section of the base 720 may be substantially circular; however, other suitable cross-sectional shapes, for example, cylindrical, elliptical, oval, polygon, irregular, etc., may be employed. The media 710 (i.e., the base 720, the arms 722, the contact members 724, or any combination thereof) and the media 810 may optionally be configured to transition from a collapsed state to an expanded state. That is, similarly to media 510 described above, media 710 and/or, 810 may include an expandable polymer (e.g., expandable element) which expands radially outward once the media 710 and/or 810 are deployed in an airway, e.g., after coming in contact with humidity in the airway. The media 710 and 810 are designed to ensure minimal contact with the airway wall in any orientation of the media 710, 810 within the airway 504.

Both media 710 and media 810 are configured to have minimal impact on cilia, which removes foreign particles and mucus from the lungs. Similarly to media 510, described above, media 710 and 810 may be deployed in batches. Any number of batches of the media 710, 810 useful to maintain airway patency may be deployed. Additionally, it is understood that the batches, e.g. the first and second batches of media 710, 810, may be sized differently. That is, the first batch of media 710, 810 may have a first dimension (e.g., diameter) whereas the second batch of media 710, 810 may have a second dimension (e.g., diameter) larger than the first dimension. The dimensions of the batches of media 710, 810 may be selected such that upon deployment in the airway, the media 710, 810 promote airflow in the airway. Additionally or alternatively, the dimensions of media 710, 810 may be selected such that upon deployment in the airway, a plurality of media 710, 810 may be configured to interlock and span the airway so as to collectively promote airflow in the airway. In this way, progressively larger media 710, 810 may be introduced into airway to open-up progressively larger portions of airway. Said differently, smaller media 710, 810 (e.g., media 710, 810 in a first batch) may travel further distally through airway of a patient while larger media 710, 810 (e.g., media 710, 810 in a second batch) may not travel as far. In some exemplary embodiments, the base 720 may be partially biodegradable so that a lumen and or passageway through base 720 (not shown) is created after a period of time and to further reduce interaction with the cilia.

Figure 9:
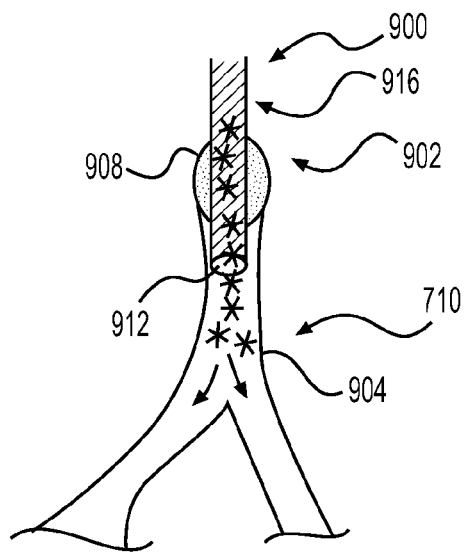
FIG. 9 illustrates a device for deploying the exemplary media of FIG. 7 in the airway of an unhealthy lung according to the second embodiment of the present disclosure.

FIG. 9 illustrates a device 900 for deploying the exemplary media 710 of FIG. 7 (or the exemplary media 810 of FIG. 8) in the airway 904 of a lung suffering from, for example, COPD according to a second exemplary embodiment of the present disclosure. The device 900 includes a deployment member 902 configured for insertion into or proximate airways 904 in communication with a diseased portion of a lung of a patient. The deployment member 902 may be a steerable delivery catheter, such as a balloon catheter 916, but other types of known, related art, or later developed steerable delivery catheters can be used to target particular diseased regions of unhealthy lungs. The deployment member 902 may have a cross-sectional configuration adapted to be received in the airway 904. The cross-section of the deployment member 902 may be substantially circular; however, other suitable cross-sectional shapes, for example, elliptical, oval, polygon, irregular, etc., may be employed.

The balloon catheter 916 includes a balloon 908 configured to transition between a first substantially deflated configuration and a second substantially expanded configuration. The balloon catheter 916 may be introduced into or proximate the airway 904 in communication with a diseased portion of a lung while in the first substantially deflated configuration. Upon reaching a targeted location within or proximate a selected airway 904, the balloon 908 may be inflated via an inflation lumen (not shown) extending through balloon catheter 916 such that balloon 908 expands to the second substantially expanded configuration and contacts an inner surface of the selected airway 904. In this way, balloon 908 may stabilize balloon catheter 916 and prevent media 710, 810 from travelling up the airway 904, proximally of the balloon 908.

In an exemplary embodiment, the balloon catheter 916 includes one or more lumens 912 extending from the distal end to a proximal portion (not shown) of the balloon catheter 916. At least one lumen 912 is configured to deploy media 710, 810 therethrough. For example, the lumen 912 may be configured to deliver a plurality of media 710, 810 in batches. That is, lumen 912 may deliver a first batch (i.e., plurality) of media 710, 810 substantially simultaneously, and subsequently, lumen 912 may deliver a second batch (i.e., plurality) of media 710, 810 substantially simultaneously. Each batch may include any number of media 710, 810. For example, each batch may include a few, hundreds, or even thousands of media 710, 810. Also, in this context, it is understood that substantially simultaneously includes a single or continuous activation of deployment member 902 which delivers media 710, 810 from the lumen 912, although not all media 710, 810 may exit the distal end of lumen 912 at the exact same time. For example, a user may activate the deployment member 902 a first time, so as to deploy a first batch (i.e., plurality) of media 710, 810. Then, a user may activate the deployment member 902 a second time (or any number of additional times), so as to deploy a second batch (i.e., plurality) of media 710, 810. Optionally, deployment member 902 may be configured to deliver media 710, 810 via a pressurized fluid source (not shown). That is, deployment member 902 may be in communication with a pressurized fluid (e.g., air) which may be fluidly coupled to lumen 912 such that the pressurized fluid may aid in moving media 710, 810 out of the distal end of lumen 912. That is, the source of pressurized fluid may assist in "pushing" media 710, 810 out of the lumen 912, thereby achieving better penetration depth of the media 710, 810 into the airway 904.

Figure 10:
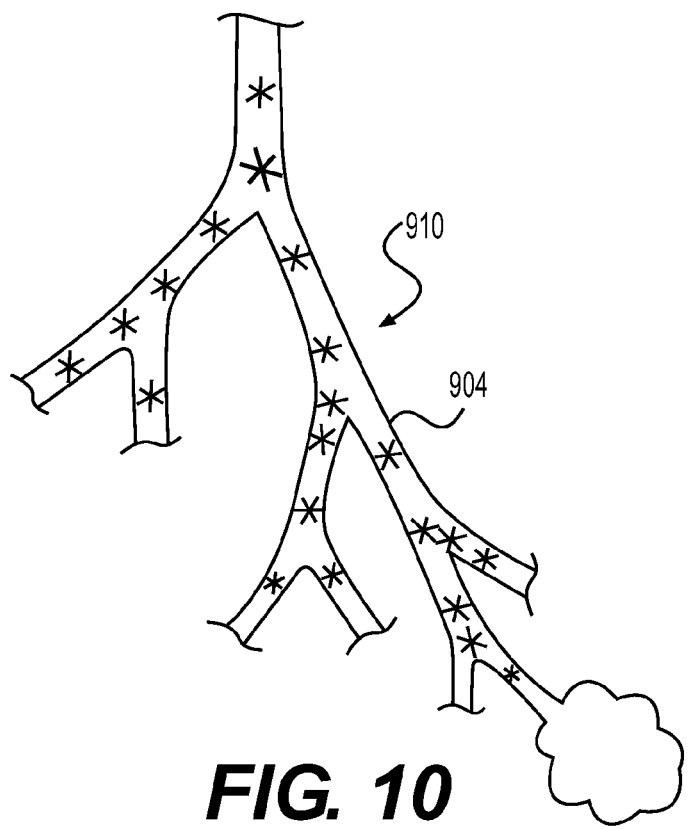
FIG. 10 illustrates the exemplary media of FIG. 7 deployed in the airway of the lung of FIG. 9 according to the second embodiment of the present disclosure.
Figure 11:
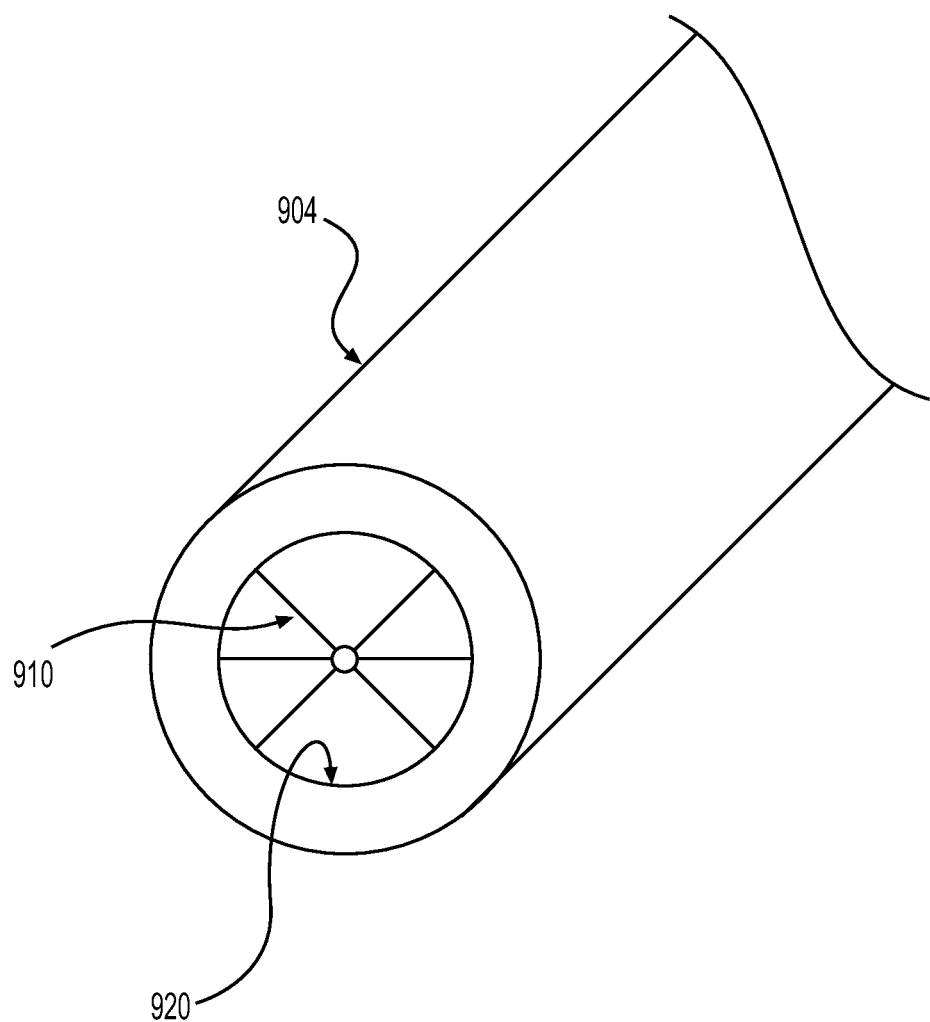
FIG. 11 illustrates a schematic illustration of the exemplary media of FIG. 7 in the lung airway according to the second embodiment of the present disclosure.

Due to the shape of the media 710, 810, it can be rapidly deployed since it supports the airway 904 in an open position regardless of its orientation (shown in FIG. 10). Additionally, the design of the media 710, 810 allows it have minimal contact with cilia the inner diameter 920 of the airway 904 in a given cross-section plane (shown in FIG. 11). However, a media, such as the media 810, can also be used for this purpose. The media 710 and the media 810 can be made of the same or different materials and be drug-eluting similarly to media 510 discussed above.

In yet another exemplary embodiment, a device, such as the devices 500, 900, can be configured to deploy the media 510, 710, 810 in any combination into an airway, such as the bronchi 110 and bronchioles 112, for treatment of the lung and, for example, the treatment of COPD. The deployed media 510, 710, 810 may be of variable sizes in order to treat airways of varying size (e.g., varying diameter).

Although the exemplary embodiments described above have been disclosed in connection with devices for manipulating lung airways, those skilled in the art will understand that the principles set out above can be applied to any bronchial device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Moreover, while specific exemplary embodiments may have been illustrated and described herein, it should be appreciated that combinations of the above embodiments are within the scope of the disclosure. Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A device for treating lung disease, comprising:
    a first plurality of media configured for deployment into one or more airways of the lung, each of the first plurality of media including a buckey-ball having a porous frame surrounding a hollow core, and each of the first plurality of media having a first diameter;
    a second plurality of media configured for deployment into the one or more airways of the lung, each of the second plurality of media including a buckey-ball having a porous frame surrounding a hollow core, and each of the second plurality of media having a second diameter smaller than the first diameter; and
    a deployment member configured for insertion into the one or more airways of the lung, the deployment member being configured to deploy each of the first plurality of media substantially simultaneously, and the deployment member being configured to deploy each of the second plurality of media substantially simultaneously;
    wherein each of the first and second pluralities of media are configured to be retained within the one or more airways of the lung.

2. The device of claim 1, wherein at least one of the first plurality of media and/or at least one of the second plurality of media includes an expansion element such that upon activation, the at least one of the first plurality of media and/or the at least one of the second plurality of media radially expands.

3. The device of claim 1, wherein each of the first and second pluralities of media is a flow-through media such that upon deployment, the first and second pluralities of media are configured to allow the passage of air through the one or more airways in which the media are retained.

4. The device of claim 1, further including:
a third plurality media configured for deployment into the one or more airways of the lung, the deployment member being further configured to deploy each of the third plurality of media substantially simultaneously.

5. The device of claim 1, wherein the deployment member includes a balloon catheter.

6. The device of claim 1, wherein each of the first plurality of media and each of the second plurality of media is an expandable member configured to expand radially outward as a result of contacting humidity in the one or more airways.

7. A method for treating lung disease, comprising:
inserting a deployment member into or proximate one or more airways of the lung;
deploying a first plurality of media configured for deployment into a portion of the lung substantially simultaneously, wherein at least some of the first plurality of media are retained and come to rest at a first position in a first lung airway such that air may travel through the first plurality of media at the first position and through the first lung airway, after the first plurality of media is at rest in the first airway; and
deploying a second plurality of media configured for deployment into the one or more airways of the lung substantially simultaneously, wherein each of the second plurality of media has a smaller diameter than each of the first plurality of media, at least some of the second plurality of media are retained and come to rest at a second position in a second lung airway that is distal to the first lung airway and has a smaller diameter than the first lung airway, such that air may travel through the second plurality of media at the second position and through the second lung airway, after the second plurality of media is at rest in the second airway.

8. The method of claim 7, wherein, after the first plurality of media is at rest in the first airway, air may travel through the first plurality of media during both inhalation and exhalation of the lung, and after the second plurality of media is at rest in the second airway, air may travel through the second plurality of media during both inhalation and exhalation of the lung.

9. The method of claim 8, wherein each of the first plurality of media and each of the second plurality of media includes a porous frame surrounding a hollow core.

10. The method of claim 9, wherein the porous frame is an expandable member configured to expand radially outward as a result of contacting humidity in the one or more airways.

11. The method of claim 7, wherein each of the first plurality of media is configured to elute a bronchodilator.

* * * * *